United States Patent
On

(10) Patent No.: US 6,319,514 B1
(45) Date of Patent: Nov. 20, 2001

(54) ANALGESIC AND ANTI-INFLAMMATORY COMPOSITIONS COMPRISING DOMPERIDONE AND METHODS OF USING SAME

(75) Inventor: Ninh On, London (GB)

(73) Assignee: The Boots Company, PLC, Nottingham (GB)

( * ) Notice: Subject to any disclaimer, the term of this patent is extended or adjusted under 35 U.S.C. 154(b) by 0 days.

(21) Appl. No.: 09/492,164

(22) Filed: Jan. 27, 2000

Related U.S. Application Data

(63) Continuation of application No. 08/859,185, filed on Jun. 20, 1997.

(30) Foreign Application Priority Data

Jun. 26, 1996 (GB) .................................................. 9613410

(51) Int. Cl.⁷ ................ A61K 9/02; A61K 9/16; A61K 9/50; A61K 31/192; A61K 31/5415

(52) U.S. Cl. ................... 424/436; 424/451; 424/464; 424/466; 424/474; 424/490; 514/225.2; 514/568; 514/557

(58) Field of Search .................... 424/474, 436, 424/451, 466, 490; 514/322

(56) References Cited

U.S. PATENT DOCUMENTS

| | | | |
|---|---|---|---|
| 4,983,621 | * | 1/1991 | Bunce et al. . |
| 5,053,429 | * | 10/1991 | Hirsch et al. . |
| 5,587,179 | * | 12/1996 | Gergely et al. . |
| 5,891,885 | * | 4/1999 | Caruso . |
| 5,985,874 | * | 11/1999 | Owen et al. . |

OTHER PUBLICATIONS

Postgraduate Medical Journal; "Headache", Ruth Atkinson, M.D. and Otto Appenzeller, M.D., Ph.D., 60:841–846, (Dec. 1984).*
J. Clin Pharmacol, Therapeutic Review, "Current Concepts of Migraine Therapy", Seymour Diamond, M.D. and Ellen Millstein, M.D., 28:193–199, (1988).*
The Medical Letter, On Drugs and Therapeutics; "Drugs for Migraine", vol. 26, Issue 673, pp. 95–96 (Oct. 26, 1984).*
Br Med. J, "Treating Migraine", C. Clough, vol. 299, pp. 141–142 (Jul. 15, 1989).*
Practical Therapeutics, "Migraine, Current Concepts of Pathogenesis and Treatment", Richard Peatfield, Drugs 26:364–371, (1983).*
Br. Med. J, "Sumatriptan in Migraine", JMS Pearce, vol. 303 (Dec. 14, 1991).*
The Annals of Pharmacotherapy, "Sumatriptan: A Selective 5–Hydroxytryptamine Receptor Agonist For The Acute Treatment of Migraine", Terence Fullerton and Fran M. Gengo, vol. 26, pp. 800–808, (1992).*

Eur Neurol, "A Study to Compare Oral Sumatriptan with Oral Aspirin plus Oral Metoclopramide in the Acute Treatment of Migraine", Ms. C.J. Thomson, Study Coordinator, 32:177–184 (1992).*
Cephalalgia, "Domperidone Plus Paracetamol in the Treatment of Migraine", E. Anne MacGregor, et al., 13(2):124–127 (1993).*
Therapia. Hungarica, "The Role of a Peripheral Dopamine–Antagonist (Motilium) in Improving the Tolerance t Steroidal and Non–Steroidal Anti–Inflammatory Agents", Z. Zahumensky, et al., vol. 38, pp. 156–159 (1990).
The Pharmaceutical Journal, "Migraine–Separate Administration of Antiemetic and Analgesic Drugs Recommended", p. 654, (Nov. 26, 1983).
Deutsche Apotheker Zeltung, "Selbstmedikation bei Migraene and Kopfschmerz vom Spannugstyp", H. Goebel-vol. et al., 135, No. 9 (Mar. 2, 1995).
Nuova Rivista di Neurologia, "Linee–guida per il Trattamento Dell'attacco Acuto", Franco Granella, Suppl. al vol. 5, No. 6 (Dec. 1995).
Meunch. Med. Wahr, "Therapie des Medikamenteninduzierten Dauerkopfschmerzes", H.C. Diener et al., vol. 134, No. 10, pp. 159–162 (1992).
Abstract of Schmerz, "Medical Therapy for Menstrual Migraine", V. Pfaffenrath et al., vol. 10, No. 3, pp. 146–148 (1996).
Abstract of Acta. Clin., "Pharmacology of Migraine", V. Demarin et al., vol. 32, No. 2, pp. 81–89 (1995).
Abstract of Internist, "Pain Therapy in Chronic Headache and Migraine", H.C. Diener, vol. 35, No. 1, pp. 26–31 (1994).
Abstract of Pain, "Behavioural and Prophylactic Pharmacological Intervention Studies of Pediatric Migraine: An Exploratory Meta–analysis", C. Hermann et al., vol. 60, No. 3, pp. 329–356 (1995).

(List continued on next page.)

Primary Examiner—Diana Dudash
Assistant Examiner—Alysia Berman
(74) Attorney, Agent, or Firm—Arent Fox Kintner Plotkin & Kahn, PLLC

(57) ABSTRACT

The present invention provides a method for eliciting an onset hastened analgesic and anti-inflammatory response and combating nausea in acute migraine attacks. This method comprises administering a pharmaceutical composition comprising more than one active ingredient, wherein said more than one active ingredient consist essentially of:

(i) domperidone or an analogue thereof in an amount sufficient to hasten the onset of the analgesic and anti-inflammatory response and to combat nausea in an acute migraine attack, and (ii) a NSAID, a pharmaceutically acceptable salt thereof or a pure (–) or pure (+) optical isomeric form thereof in an analgesically and anti-inflammatory effective amount, wherein said NSAID is selected from the group consisting of proprionic acid derivatives, acetic acid derivatives, fenamic acid derivatives, biphenylcarboxylic acid derivatives and oxicams.

95 Claims, No Drawings-

OTHER PUBLICATIONS

Abstract of Cephalagia, "*Analgesics and NSAIDs in the Treatment of the Acute Migraine Attack*", V. Pfaffenrath et al., Suppl. 15, vol. 15, pp. 14–20 (1995).

Abstract of Eur–Neurol., "*A Review of Current Treatments for Migraine*", H.C. Diener, Suppl. 2, vol. 34, pp. 18–25 (1994).

Abstract of Scott Med J., "Migraine—Treatment of Acute Attack", M. Wilkinson, vol. 30, No. 4, pp 258–262 (1985).

Abstract of Cephalagia, "Treatment of the Acute Migraine Attack—Current Status", vol. 3, No. 1, pp 61–67 (1983), M. Wilkinson.

* cited by examiner

ANALGESIC AND ANTI-INFLAMMATORY COMPOSITIONS COMPRISING DOMPERIDONE AND METHODS OF USING SAME

This is a continuation application of U.S. patent application Ser. No. 08/859,185, filed Jun. 20, 1997, the disclosure of which is incorporated by reference.

BACKGROUND TO THE ART

The current means of combating migraine attacks include simple analgesics such as aspirin or other nonsteroidal anti-inflammatory drugs (NSAIDS) and paracetamol, taken at the earliest signs of an attack [1,2,3]. Aspirin, paracetamol and phenacetin have long been among the most commonly used members of the NSAIDS class. Amongst the newer NSAIDS are ibuprofen, ketoprofen, mefenamic acid, diflunisal, naproxen and piroxicam. The most widely used NSAIDS available over the counter that have fewer gastro intestinal side effects than aspirin are paracetamol and ibuprofen.

Combined preparations of paracetamol or aspirin with an anti-emetic agent such as buclizine or metoclopramide, have been used to alleviate the nausea symptoms that often accompanied a migraine attack. Commercially, they are available as Migraleve Duo®, Paramax®, Migravess®. Narcotic analgesics such as codeine have also been employed together with NSAIDS to obtain synergistic analgesia, for example Migraleve Yellow®, co-codamol.

Gastric stasis, commonly present in migraine[4], causes the poor absorption of the analgesics. Dispersible and effervescent formulations have been used in an attempt to overcome this [4]. Metoclopramide, an anti-emetic, also relieves gastric stasis which has been found useful counteracting the reduced analgesic effects of paracetamol in migraine attacks [1,4,5].

Attacks who do not respond to analgesics may be treated with ergot preparations such as ergotamine tartrate. Newer alternatives to ergot compounds for acute migraine are the selective serotonin 5HT1 agonist, for example Sumatriptan® [6,7]. Recent trials reported that oral 100 mg sumatriptan to be as effective as aspirin 900 mg plus 10 mg metoclopramide for initial attacks and more effective in subsequent attacks [8].

The use of metoclopramide combined with either paracetamol, or aspirin has already been disclosed. Domperidone is a dopamine antagonist but is less likely than metoclopramide to produce extra pyramidal side effects since it does not cross the blood brain barrier. It stimulates gastro-intestinal mobility and is used in the management of nausea and vomiting. The activity of domperidone on the gastro intestinal mobility could enhance the rate of absorption of the analgesics. In Cephalagia 13 (2), 124–7 (1993), the safety and efficacy of separately administered domperidone in combination with paracetamol in the treatment of acute attack of migraine was demonstrated. The method of making a film coated tablet containing paracetamol and domperidone is disclosed in WO95/22974.

As far as the inventor knows, the art has never suggested that domperidone either be added to selected NSAIDS, which differ substantially in chemical structure from paracetamol; or be added to selected NSAIDS together with selected narcotic analgesic drugs. Also, the prior art does not suggest the use of any two-component composition of a selected NSAID and domperidone; and three-component of a selected NSAID, a selected narcotic analgesic and domperidone to hasten the analgesic response and to manage nausea symptoms in migraine attacks.

DETAILED DESCRIPTION OF THE INVENTION

The NSAIDS for use in the compositions and methods of the present invention can be selected from the following categories:

1) the propionic acid derivatives
2) the acetic acid derivatives;
3) the fenamic acid derivatives;
4) the biphenylcaboxylic acid derivatives;
5) the oxicams.

All the contemplated compounds can be used at appropriate dosage levels for the purpose in the composition of the present invention. The compounds in groups 1 to 4 typically contain a carboxylic acid function; however, those acids are sometimes administered in the form of their pharmaceutically acceptable salts, e.g. sodium salts.

The propionic acid derivatives for use herein include, but are not limited to, ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, and bucloxic acid. Structurally related propionic acid derivatives having similar analgesic and anti-inflammatory properties are also intended to be encompassed by this group. Presently preferred members of the propionic acid group include ibuprofen, naproxen, flurbiprofen, fenoprofen, ketoprofen and fenbufen.

The acetic acid derivatives for use herein include, but not limited to, indomethacin, sulindac, tolmetin, zomepirac, diclofenac, fenchlofenac, alchlofenac, ibufenac, isoxepac, furofenac, tiopinac, zidometacin, acemetacin, fentiazac, clidanac and oxipinac. Structurally related acetic acid derivatives having similar analgesic and anti-inflammatory properties are also intended to be encompassed by this group. Presently, preferred members of the acetic acid group include tolmetin sodium, zomepinac sodium, sulindac and indomethacin.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to encompassed by this group. Presently, preferred members of the fenamic acid group include mefenamic acid and meclofenamate sodium (meclofenamic acid, sodium salt).

The biphenylcarboxylic acid derivatives for use herein include, but are not limited to, diflunisal and flufenisal. Structurally related biphenylcarboxylic acid derivatives having similar analgesic and anti-inflammatory properties are also intended to be encompassed by this group. Preferred members of this group are diflunisal and flufenisal.

The oxicams for use herein include, but are not limited to, piroxicam, sudoxicam, isoxicam. Structurally related oxicams having similar analgesic and anti-inflammatory properties are also intended to be encompassed by this group. A preferred member of this group is piroxicam.

The narcotic analgesics for use in the present invention are orally active narcotic agonists. Suitable agonist-antagonist for use herein include orally analgesically active antagonists of the nalorphine type, notably pentazocine; and orally analgesically active antagonists of the morphine type, notably buprenorphine. Another suitable agonist-antagonist is meptazinol. Suitable narcotic agonists for use herein include orally analgesically active members of the morphine group, notably codeine, oxycodone, dihydrocodeine, dextropropoxyphene, papaveretum and tramadol. In many instances, the narcotic analgesics for use herein are administered in the forms of their pharmaceutically acceptable acid addition salts, e.g. codeine sulphate, codeine phosphate, dihydrocodeine tartrate and tramadol hydrochloride. Structurally related analogues to the aforementioned compounds having similar analgesic property are also intended to be encompassed by this group.

For compounds (NSAIDS or narcotic analgesics) which have optically active centre(s), the invention refers to the racemate as well as the pure (−) or (+) optical isomeric forms.

The domperidone or its analogues used herein is intended to encompass not only domperidone as the anhydrous powder but any salt or derivatives or any compounded mixture thereof which is non toxic, pharmaceutically acceptable and which has gastric motility stimulating activity to enhance absorption of the co-administered analgesic(s) in gastric stasis and anti-emetic property. Presently, the preferred salt of domperidone is maleate.

The term "selected NSAID" as used herein is intended to mean any non-narcotic analgesic/nonsteroidal anti-inflammatory compound within one of the five structural categories indicated hereinabove. Similarly, the term "selected narcotic analgesic" as used herein is intended to mean any orally analgesically active narcotic analgesic, be it an orally active narcotic agonist having oral analgesic activity. The terms "selected NSAID" and "selected narcotic analgesic" are used for the sake of simplicity in the discussion which follows.

When a selected NSAID or NSAID plus a selected narcotic analgesic is combined with domperidone in accord with the present invention, the following results may be produced:

The analgesic/anti-inflammatory effect of the selected NSAID as a single active or NSAID plus a selected narcotic analgesic can be brought on more quickly;

the nausea symptom experienced in acute migraine attacks can be averted or alleviated.

For patients suffering migraine headache, the time from administration of medication to the onset of effective relief is clearly of paramount importance. The hastening of the onset analgesia by combining domperidone with a selected NSAID or a selected NSAID plus a selected narcotic analgesic according to the present invention is therefore can be very significant.

The precise amount of NSAID or narcotic analgesic drug for use in the present compositions will vary depending, for example, on the specific drug chosen, the condition for which the drug is administered. Generally speaking, the selected NSAID or narcotic analgesic can be employed in any amount known to be an effective analgesic and anti-inflammatory amount.

Typical effective analgesic amounts of presently preferred NSAIDs/narcotic analgesic for use in unit dose compositions of the invention can be found in the British National Formulary, American Hospital Formulary, Martindale Extra Pharmacopoeia, e.g. 50–600 mg Ibuprofen. In a two component composition of a selected NSAID and domperidone and a three component composition of a selected NSAID, a selected narcotic analgesic and domperidone, the daily analgesic dose for each analgesic will generally not exceed their daily analgesic dosages. The ratio of a selected NSAID to a selected narcotic analgesic may vary depending on the particular drugs selected and the required analgesic response.

While the compositions of the invention are preferably for oral use, they may also be formulated for and administered by other methods which are known for administering analgesics, e.g. suppositories. Also, the preferred dosage levels mentioned earlier are used in adults; paediatric compositions would contain proportionally less of the active ingredients.

The compositions of the present invention can be conveniently administered by any route of administration suitable for the selected NSAID and/or selected narcotic analgesic component, e.g. oral or rectal. Preferably, the combination is formulated with any suitable nontoxic pharmaceutically acceptable inert carrier material. Such carrier materials are well known to those skilled in the art.

In a typical preparation for oral administration, e.g. tablet or capsule, the selected NSAID in an effective analgesic/anti-inflammatory amount and domperidone in an amount sufficient to hasten its onset and/or to control nausea and vomiting; or the selective NSAID in an effective analgesic/anti-inflammatory amount together with a selected narcotic analgesic in an amount sufficient to enhance the analgesic response and domperidone in an amount sufficient to hasten its onset and/or to control nausea and vomiting; are combined with any oral nontoxic pharmaceutically acceptable inert carrier such as lactose, starch (pharmaceutical grade), dicalcium phosphate, calcium sulphate, kaolin, mannitol and powder sugar.

Additionally, when required, suitable binders, lubricants, disintegrating agents, colouring agents and coating agents can also be included. Typical binders include starch, gelatine, sugars such as sucrose, molasses and lactose, natural and synthetic gums such as acacia, sodium alginate, carboxymethylcellulose, methylcellulose, polyvinylpyrrolidone, polyethylene glycol, ethylcellulose and waxes. Typical lubricants for use in the dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulphate. Sweetening and flavouring agents and preservatives may be included, particularly when a liquid dosage form is formulated, e.g. syrup, suspension and elixir. When the dosage form is a capsule, it may contain, in addition to the above type, a liquid carrier such as fatty oil. Various other materials may be present as coatings or to otherwise modify the physical form of the dosage unit.

REFERENCES

1) Atkinson R, Appenzeller O (1984). Headache. Postgrad Med J; 60: 841–846.
2) Diamond S, Milistein E (1988). Current concepts of migraine therapy. J. Clin Pharmacol; 28: 193–199.
3) Anonymous (1984). Drugs for migraine. Med Lett Drugs Ther; 26: 95–96.
4) Clough C (1989). Treating migraine. Br Med J; 299: 141–142.
5) Peatfield R (1983). Migraine: Current concepts of pathogenesis and treatment. Drugs; 26: 364–371.
6) Pearce JMS (1991). Sumatriptan in migraine. Br Med J; 303: 1941.
7) Fullerton T, Gengo F M (1992). Sumatriptan: a selective 5-hydroxytryptamine receptor agonist for the acute treatment of migraine. Ann Pharmacother; 26: 800–808.
8) The oral Sumatriptan and Aspirin plus Metoclopramide Comparative Study Group (1992). A study to compare oral sumatriptan with oral Aspirin plus oral metoclopramide in the acute treatment of migraine. Eur Neurol; 32:177–184.

What is claimed is:

1. A method for eliciting an onset hastened analgesic and anti-inflammatory response and combating nausea in acute migraine attacks in a subject in need of an analgesic, anti-inflammatory and anti-nausea response, comprising administering a pharmaceutical composition comprising effective amounts of more than one active ingredient to said subject, wherein said more than one active ingredient consist essentially of:
   (i) domperidone or an analogue thereof in an amount sufficient to hasten the onset of the analgesic and anti-inflammatory response and to combat nausea in an acute migraine attack,
   (ii) a NSAID, a pharmaceutically acceptable salt thereof or a pure (−) or (+) optical isomeric form thereof in an analgesically and anti-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenec, alclofenac, ibufenac, isoxepac, furofenac, tiopinac, zidometacin, acemetacin, fentiazac, clidanac, oxipinac, mefenamic acid, meclofenamic acid, flufenamic acid, niflumic acid, tolfenamic acid, diflunisal, flufenisal, piroxicam, sudoxicam and isoxicam; and
   (iii) a narcotic analgesic, or a pharmaceutically acceptable salt thereof or a pure (−) or (+) pure optical isomer thereof in an analgesically effective amount.

2. A pharmaceutical composition for eliciting an onset hastened analgesic and anti-inflammatory response and combating nausea in acute migraine attacks comprising more than one active ingredient, wherein said more than one active ingredient consist essentially of:
   (i) domperidone or an analogue thereof in an amount sufficient to hasten the onset of the analgesic and anti-inflammatory response and to combat nausea in an acute migraine attack,
   (ii) a NSAID, a pharmaceutically acceptable salt thereof or a pure (−) or (+) optical isomeric form thereof in an analgesically and anti-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclofenac, ibufenac, isoxepac, furofenac, tiopinac, zidometacin, acemetacin, fentiazac, clidanac, oxipinac, mefenamic acid, meclofenamic acid, flufenamic acid, niflumic add, tolfenamic acid, diflunisal, flufenisal, piroxicam, sudoxicam and soxicam; and
   (iii) a narcotic analgesic, or a pharmaceutically acceptable salt thereof or a pure (−) or pure (+) optical isomer thereof in an analgesically effective amount.

3. A pharmaceutical composition according to claim 2 wherein the domperidone analogue is domperidone maleate.

4. A pharmaceutical composition according to claim 2, wherein the NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, and bucloxic acid.

5. A pharmaceutical composition according to claim 2, wherein the NSAID is selected from the group consisting of indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxipinac.

6. A pharmaceutical composition according to claim 2, wherein the NSAID is selected from the group consisting of mefenamic acid, meclofenamic acid, flufenamic acid, niflumic acid and tolfenamic acid.

7. A pharmaceutical composition according to claim 2, wherein the NSAID is selected from the group consisting of diflunisal and flufenisal.

8. A pharmaceutical composition according to claim 2, wherein the NSAID is selected from the group consisting of piroxicam, sudoxicam and isoxicam.

9. A pharmaceutical composition according to claim 2, wherein said composition is formulated for oral administration.

10. A pharmaceutical composition according to claim 2, wherein said composition is formulated as a tablet or capsule with the addition of a suitable pharmaceutically acceptable carrier.

11. A pharmaceutical composition according to claim 10, wherein said composition is formulated as a dispersible or effervescent dosage form with the addition of a suitable pharmaceutically acceptable carrier.

12. A pharmaceutical composition according to claim 10, wherein said composition is in a microencapsulated dosage form with the addition of a suitable pharmaceutically acceptable carrier.

13. A pharmaceutical composition according to claim 2, said composition is formulated as granules for oral administration with the addition of a suitable pharmaceutically acceptable carrier.

14. A pharmaceutical composition according to claim 2, wherein said composition is formulated for rectal administration.

15. A pharmaceutical composition according to claim 14, wherein said composition is formulated as a suppository with the addition of a suitable pharmaceutically acceptable carrier.

16. A pharmaceutical composition according to claim 14, wherein said composition is formulated as an enema or rectal solution.

17. A method according to claim 1 wherein the domperidone analogue is domperidone maleate.

18. A method according to claim 1, wherein the NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, and bucloxic acid.

19. A method according to claim 1, wherein said composition is formulated for oral administration.

20. A method according to claim 1, wherein said composition is formulated as a tablet or capsule.

21. A method according to claim 19, wherein said composition is formulated as a dispersible or effervescent dosage form.

22. A method according to claim 19, wherein said composition is in microencapsulated dosage form.

23. A method according to claim 1, wherein said composition is formulated as granules for oral administration.

24. A method according to claim 1, wherein said composition is formulated for rectal administration.

25. A method according to claim 24, wherein said composition is formulated as a suppository.

26. A method according to claim 24, wherein said composition is formulated as an enema or rectal solution.

27. A method for eliciting an onset hastened analgesic and anti-inflammatory response in acute migraine attacks in a subject in need of the analgesic and anti-inflammatory response, comprising administering a pharmaceutical composition comprising effective amounts of more than one active ingredient to said subject, wherein said more than one active ingredient consist essentially of:
(i) domperidone or an analogue thereof in an amount sufficient to hasten the onset of the analgesic and anti-inflammatory response in an acute migraine attack,
(ii) a NSAID, a pharmaceutically acceptable salt thereof or a pure (−) or (+) optical isomeric form thereof in an analgesically and anti-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclofenac, ibufenac, isoxepac, furofenac, tiopinac, zidometacin, acemetacin, fentiazac, clidanac, oxipinac, mefenamic acid, meclofenamic acid, flufenamic acid, niflumic acid, tolfenamic acid, diflunisal, flufenisal, piroxicam, sudoxicam and isoxicam; and
(iii) a narcotic analgesic, or a pharmaceutically acceptable salt thereof or a pure (−) or (+) pure optical isomer thereof in an analgesically effective amount.

28. A method according to claim 27 wherein the domperidone analogue is domperidone maleate.

29. A method according to claim 27, wherein the NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, and bucloxic acid.

30. A method according to claim 27, wherein the NSAID is selected from the group consisting of indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxipinac.

31. A method according to claim 27, wherein the NSAID is selected from the group consisting of mefenamic acid, meclofenamic acid, flufenamic acid, niflumic acid and tolfenamic acid.

32. A method according to claim 27, wherein the NSAID is selected from the group consisting of diflunisal and flufenisal.

33. A method according to claim 27, wherein the NSAID is selected from the group consisting of piroxicam, sudoxicam and isoxicam.

34. A method according to claim 27, wherein said composition is formulated for oral administration.

35. A method according to claim 34, wherein said composition is formulated as a tablet or capsule with the addition of a suitable pharmaceutically acceptable carrier.

36. A method according to claim 34, wherein said composition is formulated as a dispersible or effervescent dosage form with the addition of a suitable pharmaceutically acceptable carrier.

37. A method according to claim 34, wherein said composition is in microencapsulated dosage form with the addition of a suitable pharmaceutically acceptable carrier.

38. A method according to claim 34, wherein said composition is formulated as granules for oral administration.

39. A method according to claim 27, wherein said composition is formulated for rectal administration.

40. A method according to claim 39, wherein said composition is formulated as a suppository with the addition of a suitable pharmaceutically acceptable carrier.

41. A method according to claim 39, wherein said composition is formulated as an enema or rectal solution with the addition of a suitable pharmaceutically acceptable carrier.

42. A pharmaceutical composition for eliciting an onset hastened analgesic and anti-inflammatory response in acute migraine attacks comprising effective amounts of more than one active ingredient to said subject, wherein said more than one active ingredient consist essentially of:
(i) domperidone or an analogue thereof in an amount sufficient to hasten the onset of the analgesic and anti-inflammatory response in an acute migraine attack,
(ii) a NSAID, a pharmaceutically acceptable salt thereof or a pure (−) or (+) optical isomeric form thereof in an analgesically and anti-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclotenac, ibufenac, isoxpac, furofenac, tiopinac, zidometacin, acemetacin, fentiazac, clidanac, oxipinac, mefenamic acid, meclofenamic acid, flufenamic acid, niflumic acid, tolfenamic acid, diflunisal, flufenisal, piroxicam, sudoxicam and isoxicam; and
(iii) a narcotic analgesic, or a pharmaceutically acceptable salt thereof or a pure (−) or (+) pure optical isomer thereof in an analgesically effective amount.

43. A composition according to claim 42 wherein the domperidone analogue is domperidone maleate.

44. A composition according to claim 42, wherein said composition is formulated for oral administration.

45. A composition according to claim 44, wherein said composition is formulated as a tablet or capsule with the addition of a suitable pharmaceutically acceptable carrier.

46. A composition according to claim 44, wherein said composition is formulated as a dispersible or effervescent dosage form with the addition of a suitable pharmaceutically acceptable carrier.

47. A composition according to claim 44, wherein said composition is in microencapsulated dosage form with the addition of a suitable pharmaceutically acceptable carrier.

48. A composition according to claim 44, wherein said composition is formulated as granules for oral administration.

49. A composition according to claim 42, wherein said composition is formulated for rectal administration.

50. A composition according to claim 42, wherein said composition is formulated as a suppository with the addition of a suitable pharmaceutically acceptable carrier.

51. A composition according to claim 42, wherein said composition is formulated as an enema or rectal solution with the addition of a suitable pharmaceutically acceptable carrier.

52. A method for combating nausea in acute migraine attacks in a subject in need of an anti-nausea response, comprising administering a pharmaceutical composition comprising more than one active ingredient to said subject, wherein said more than one active ingredient consist of:
(i) domperidone or an analogue thereof in an amount sufficient to combat nausea in an acute migraine attack,
(ii) a NSAID, a pharmaceutically acceptable salt thereof or a pure (−) or (+) optical isomeric form thereof in an analgesically and anti-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclofenac, ibufenac, isoxepac, furofenac, tiopinac, zidometacin, acemetacin, fentiazac, clidanac, oxipinac, mefenamic acid, meclofenamic acid, flufenamic acid, niflumic acid, tolfenamic acid, diflunisal, flufenisal, piroxicam, sudoxicam and isoxicam; and
(iii) a narcotic analgesic or a pharmaceutically acceptable salt thereof, or a pure (−) or pure (+) optical isomer thereof in an analgesically effective amount.

53. A method according to claim 52, wherein the NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen and bucloxic acid.

54. A method according to claim 52, wherein the NSAID is selected from the group consisting of indomethacin, sulindac, tolmetin, zomepirac, diclofenac, fenclofenac, alclofenac, ibufenac, isoxepac, furofenac, tiopinac, zidometacin, acemetacin, fentiazac and oxipinac.

55. A method according to claim 52, wherein the NSAID is selected from the group consisting of mefenamic acid, meclofenamic acid, flufenamic acid, niflumic acid and tolfenamic acid.

56. A method according to claim 52, wherein the NSAID is selected from the group consisting of diflunisal and flufenisal.

57. A method according to claim 52, wherein the NSAID is selected from the group consisting of piroxicam, sudoxicam and isoxicam.

58. A method according to claim 52, wherein the NSAID is ibuprofen.

59. A method according to claim 58, wherein said more than one active ingredient consist of domperidone maleate and ibuprofen.

60. A method according to claim 52, wherein said pharmaceutical composition further comprises a suitable pharmaceutically acceptable carrier.

61. A method for combating nausea in acute migraine attacks in a subject in need of an anti-nausea response, comprising administering a pharmaceutical composition comprising more than one active ingredient to said subject, wherein said more than one active ingredient consist of:
(i) domperidone or an analogue thereof in an amount sufficient to combat nausea in an acute migraine attack;
(ii) a NSAID, a pharmaceutically acceptable salt thereof or a pure (−) or (+) optical isomeric form thereof in an analgesically and anti-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclofenac, ibufenac, isoxepac, furofenac, tiopinac, zidometacin, acemetacin, fentiazac, clidanac, oxipinac, mefenamic acid, meclofenamic acid, flufenamic acid, niflumic acid, tolfenamic acid, diflunisal, flufenisal, piroxicam, sudoxicam and isoxicam; and
(iii) a narcotic analgesic or a pharmaceutically acceptable salt thereof, or a pure (−) or pure (+) optical isomer thereof in an analgesically effective amount.

62. A method according to claim 61, wherein the NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen and bucloxic acid.

63. A method according to claim 61, wherein the NSAID is selected from the group consisting of indomethacin, sulindac, tolmetin, zomepirac, diclofenac, fenclofenac, alclofenac, ibufenac, isoxepac, furofenac, tiopinac, zidometacin, acemetacin, fentiazac and oxipinac.

64. A method according to claim 61, wherein the NSAID is selected from the group consisting of mefenamic acid, meclofenamic acid, flufenamic acid, niflumic acid and tolfenamic acid.

65. A method according to claim 61, wherein the NSAID is selected from the group consisting of diflunisal and flufenisal.

66. A method according to claim 61, wherein the NSAID is selected from the group consisting of piroxicam, sudoxicam and isoxicam.

67. A method according to claim 61, wherein the NSAID is ibuprofen.

68. A method according to claim 67, wherein said more than one active ingredient consist of domperidone maleate, ibuprofen and a narcotic analgesic or a pharmaceutically acceptable salt thereof, wherein said narcotic analgesic or a pharmaceutically acceptable salt thereof is selected from the group consisting of codeine sulfate, codeine phosphate, dihydrocodeine tartrate and tramadol hydrochloride.

69. A method according to claim 61, wherein said pharmaceutical composition further comprises a suitable pharmaceutically acceptable carrier.

70. A pharmaceutical composition for combating nausea in acute migraine attacks, comprising more than one active ingredient, wherein said more than one active ingredient consist of:
(i) domperidone or an analogue thereof in an amount sufficient to combat nausea in an acute migraine attack,
(ii) a NSAID, a pharmaceutically acceptable salt thereof or a pure (−) or (+) optical isomeric form thereof in an analgesically and ant-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclofenac, ibufenac, isoxepac, furofenac, tiopinac, zidometacin, acemetacin, tentiazac, clidanac, oxipinac, mefenamic acid, meclofenamic acid, flufenamic acid, niflumic acid, tolfenamic acid, diflunisal, flufenisal, piroxicam, sudoxicam and isoxicam, fenamic acid derivatives, biphenylcarboxylic acid derivatives and oxicams; and
(iii) a narcotic analgesic or a pharmaceutically acceptable salt thereof, or a pure (−) or pure (+) optical isomer thereof in an analgesically affective amount.

71. A pharmaceutical composition according to claim 70, wherein the NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen and bucloxic acid.

72. A pharmaceutical composition according to claim 70, wherein the NSAID is selected from the group consisting of indomethacin, sulindac, tolmetin, zomepirac, diclofenac, fenclofenac, alclofenac, ibufenac, isoxepac, furofenac, tiopinac, zidometacin, acemetacin, fentiazac and oxipinac.

73. A pharmaceutical composition according to claim 70, wherein the NSAID is selected from the group consisting of mefenamic acid, meclofenamic acid, flufenamic acid, niflumic acid and tolfenamic acid.

74. A pharmaceutical composition according to claim 70, wherein the NSAID is selected from the group consisting of diflunisal and flufenisal.

75. A pharmaceutical composition according to claim 70, wherein the NSAID is selected from the group consisting of piroxicam, sudoxicam and isoxicam.

76. A pharmaceutical composition according to claim 70, wherein the NSAID is ibuprofen.

77. A pharmaceutical composition according to claim 76, wherein said more than one active ingredient consist of domperidone maleate and ibuprofen.

78. A pharmaceutical composition according to claim 70, further comprising a suitable pharmaceutically acceptable carrier.

79. A pharmaceutical composition for combating nausea in acute migraine attacks, comprising more than one active ingredient, wherein said more than one active ingredient consist of:
(i) domperidone or an analogue thereof in an amount sufficient to combat nausea in an acute migraine attack;
(ii) a NSAID, a pharmaceutically acceptable salt thereof or a pure (−) or (+) optical isomeric form thereof in an analgesically and anti-inflammatory effective amount, wherein said NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclofenac, ibufenac, isoxepac, furofenac, tiopinac, zidometacin, acemetacin, fentiazac, clidanac, oxipinac, mefenamic acid, meclofenamic acid, flufenamic acid, niflumic acid, tolfenamic acid, diflunisal, flufenisal, piroxicam, sudoxicam and isoxicam; and
(iii) a narcotic analgesic, a pharmaceutically acceptable salt thereof or a pure (−) or pure (+) optical isomer thereof in an analgesically effective amount.

80. A pharmaceutical composition according to claim 79, wherein the NSAID is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen and bucloxic acid.

81. A pharmaceutical composition according to claim 79, wherein the NSAID is selected from the group consisting of indomethacin, sulindac, tolmetin, zomepirac, diclofenac, fenclofenac, alclofenac, ibufenac, isoxepac, furofenac, tiopinac, zidometacin, acemetacin, fentiazac and oxipinac.

82. A pharmaceutical composition according to claim 79, wherein the NSAID is selected from the group consisting of mefenamic acid, meclofenamic acid, flufenamic acid, niflumic acid and tolfenamic acid.

83. A pharmaceutical composition according to claim 79, wherein the NSAID is selected from the group consisting of diflunisal and flufenisal.

84. A pharmaceutical composition according to claim 79, wherein the NSAID is selected from the group consisting of piroxicam, sudoxicam and isoxicam.

85. A pharmaceutical composition according to claim 79, wherein the NSAID is ibuprofen.

86. A pharmaceutical composition according to claim 85, wherein said more than one active ingredient consist of domperidone maleate, ibuprofen and a narcotic analgesic or a pharmaceutically acceptable salt thereof, wherein said narcotic analgesic or a pharmaceutically acceptable salt thereof is selected from the group consisting of codeine sulfate, codeine phosphate, dihydrocodeine tartrate and tramadol hydrochloride.

87. A pharmaceutical composition according to claim 79, further comprising a suitable pharmaceutically acceptable carrier.

88. A method according to claim 1, wherein the NSAID is ibuprofen.

89. A method according to claim 1, wherein said more than one active ingredient consist of domperidone maleate, ibuprofen and a narcotic analgesic or a pharmaceutically acceptable salt thereof, wherein said narcotic analgesic or a pharmaceutically acceptable salt thereof is selected from the group consisting of codeine sulfate, codeine phosphate, dihydrocodeine tartrate and tramadol hydrochloride.

90. A pharmaceutical composition according to claim 2, wherein the NSAID is ibuprofen.

91. A pharmaceutical composition according to claim 2, wherein said more than one active ingredient consist of domperidone maleate, ibuprofen and a narcotic analgesic or a pharmaceutically acceptable salt thereof, wherein said narcotic analgesic or a pharmaceutically acceptable salt thereof is selected from the group consisting of codeine sulfate codeine phosphate, dihydrocodeine tartrate and tramadol hydrochloride.

92. A method according to claim 27, wherein the NSAID is ibuprofen.

93. A method according to claim 27, wherein said more than one active ingredient consist of domperidone maleate, ibuprofen and a narcotic analgesic or a pharmaceutically acceptable salt thereof, wherein said narcotic analgesic or a pharmaceutically acceptable salt thereof is selected from the group consisting of codeine sulfate, codeine phosphate, dihydrocodeine tartrate and tramadol hydrochloride.

94. A pharmaceutical composition according to claim 42, wherein the NSAID is ibuprofen.

95. A pharmaceutical composition according to claim 42, wherein said more than one active ingredient consist of domperidone maleate, ibuprofen and a narcotic analgesic or a pharmaceutically acceptable salt thereof, wherein said narcotic analgesic or a pharmaceutically acceptable salt thereof is selected from the group consisting of codeine sulfate, codeine phosphate, dihydrocodeine tartrate and tramadol hydrochloride.

* * * * *